United States Patent [19]

Mason

[11] Patent Number: 5,002,880

[45] Date of Patent: Mar. 26, 1991

[54] ENZYME CATALYZED SYNTHESIS OF METHYL URETHANES

[75] Inventor: Robert W. Mason, Lake Charles, La.

[73] Assignee: Olin Corporation, Cheshire, Conn.

[21] Appl. No.: 461,721

[22] Filed: Jan. 8, 1990

[51] Int. Cl.$^5$ .................. C12P 13/00; C12P 13/02
[52] U.S. Cl. .................. 435/128; 435/197; 435/129
[58] Field of Search .................. 435/128, 129, 197

[56] References Cited

FOREIGN PATENT DOCUMENTS 1-300892 12/1989 Japan .................. 435/197

OTHER PUBLICATIONS

King et al, Biochemistry, 1987, 26, 2294–2300.
Chapman et al, Biochimica et Biophysica Acta, 527 (1978), 272–276.

Primary Examiner—Carolyn S. Elmore
Attorney, Agent, or Firm—Dale Lynn Carlson

[57] ABSTRACT

The present invention relates to a process for making an isocyanate which comprises the steps of: (a) reacting an amine with dimethyl carbonate in the presence of a hydrolase enzyme catalyst, preferably at a temperature not exceeding 50° C. to form a methyl urethane, and (b) subjecting said methyl urethane to an elevated temperature in order to thermally cleave the urethane to produce an isocyanate.

4 Claims, No Drawings

ENZYME CATALYZED SYNTHESIS OF METHYL URETHANES

Isocyanates are used as reactants in the production of polyurethane foams, elastomers, sealants, coatings, adhesives, and the like. Current commercial production of isocyanates, such as toluene diisocyanate (TDI), typically utilizes phosgene to convert the corresponding amine to the desired isocyanate. The use of phosgene is undesireable from an environmental and toxicity standpoint. Accordingly new methods of producing isocyanates which do not involve the use of phosgene would be highly desired by the isocyanate manufacturing community.

Various attempts have been made in the past to develop non-phosgene routes to produce isocyanates. By way of illustration, U.S. Pat. Nos. 4,268,683 and 4,268,684 disclose the synthesis of methyl urethanes by the reaction of dialkyl or diaryl carbonates with amines at an elevated temperature. However, the high temperatures employee cause the production of unwanted byproducts, including various N-substituted alkyl and aryl compounds. In addition, there is a substantial energy cost associated with the elevated temperatures required to produce the methyl urethanes using the reactions of these patents.

It has now been surprisingly found, in accordance with the present invention, that methyl urethanes can be synthesized by an enzyme-catalyzed reaction of amines and dimethyl carbonate in the presence of hydrolase enzyme catalysts. The methyl urethanes are then converted to isocyanates by the thermal cleavage of the urethane linkage, as is known. Thus, the present invention provides a phosgene-free route to the manufacture of isocyanates via enzyme catalysis to make a methyl urethane intermediate.

In one aspect, the present invention relates to a process for making a methyl urethane which comprises reacting an amine with dimethyl carbonate in the presence of a hydrolase enzyme catalyst (preferably at a temperature not exceeding 50° C.) to form said methyl urethane.

In another aspect, the present invention relates to a Process for making an isocyanate which comprises the steps of:

(a) reacting an amine with dimethyl carbonate in the presence of a hydrolase enzyme catalyst to form a methyl urethane, and (b) subjecting said methyl urethane to an elevated temperature in order to thermally cleave the urethane to produce an isocyanate.

This and other aspects will become apparent upon a reading of the following detailed specification.

The process of the present invention for making the desired methyl urethane is suitably conducted in the presence or absence of a solvent. Suitable solvents include, for example, toluene, hexane, methylene chloride, carbon tetrachloride and chloroform. A neat reaction in the absence of a solvent is also suitable for use if desired.

Various reaction schemes are envisioned as being useful within the scope of the present invention. For example, dry catalyst suspensions, wet suspensions of buffered catalyst in the reactant/solvent media, silica gel immobilized catalyst, and TRITON X-100 and AEROSOL OT induced micelles are illustrative examples of useful reaction systems.

The preferred enzymes for use within the scope of the present invention are hydrolase enzymes, such as esterase. Other hydrolase enzymes, such as lypases, acylase I, alpha-chymotrypsin, and urease are less preferred since they were found not to produce the desired methyl urethane under a narrow range of test conditions.

The carbonate useful as a reactant within the scope of the present invention is suitable a dialkyl or diaryl-substituted carbonate, such as, for example, dimethyl carbonate, diethyl carbonate, diphenyl carbonate, and the like. Thus, phenyl urethanes are suitably made in accordance with the present invention using a diphenyl carbonate reactant.

The methyl urethane produced in accordance with the present invention is suitably converted to an isocyanate by thermal cleavage at an elevated temperature, as is known. Suitable temperatures range from about 180° C. to about 200° C. or higher, preferably at subatmospheric pressure.

The above-mentioned patents and patent applications are specifically incorporated herein by reference in their entirety.

The following examples are intended to illustrate, but in no way limit the scope of, the present invention.

EXAMPLE 1

Preparation of methyl urethane using a wet suspension of buffered catalyst

To 1.00 ml. (1.07 g., 11.9 mmole) of dimethyl carbonate was added 0.10 ml. of pH 8.0 phosphate buffered saline containing 100 units of porcine liver esterase (EC) 3.1.1.1, a product of Sigma Chemical). This was followed by the addition of 0.5 ml(0.51 g., 5.5 mmole) of aniline. The resulting suspension was shaken for 24 hours. Capillary gas chromatographic analysis of the product liquor showed 3.2 weight % conversion of aniline to its corresponding methyl urethane.

EXAMPLE 2

Preparation of methyl urethane using a dry catalyst

Porcine liver esterase (EC 3.1.1.1, 3180 units in ammonium sulfate having a pH of 8.0, a product of Sigma Chemical) was dissolved in 0.5 ml. of chilled phosphate buffered saline at a PH of 8.0. To this solution was added, in 0.25 ml. fractions, a total of 0.75 ml. of chilled acetone. The resulting suspension was centrifuged at 500 Xg. for 10 minutes. The solvents were decanted from the catalyst pellet and the catalyst was then lyphollized. To this dried catalyst pellet was added 3.0 ml. of toluene, 1.0 ml. of dimethyl carbonate and 0.5 ml. of aniline. The reaction suspension was stirred at room temperature with periodic sample aliquots taken for gas chromatographic analysis. After six days of stirring, a 2.7 weight % conversion of aniline to the corresponding methyl urethane was measured. In a control test conducted with a substantially catalyst, but without catalyst, no measurable amount of methyl urethane was produced.

What is claimed is:

1. A process for making a methyl urethane which comprises reacting an amine with dimethyl carbonate in the presence of a porcine line esterase to form said methyl urethane.

2. A process for making an isocyanate which comprises the steps of:

(a) reacting an amine with dimethyl carbonate in the presence of a porcine line esterase to form a methyl urethane, and (b) subjecting said methyl urethane to an elevated temperature in order to thermally cleave the urethane to produce an isocyanate.

3. The process of claim 1 which is conducted at a temperature not exceeding 50° C.

4. The process of claim 2 wherein step (a) is conducted at a temperature not exceeding 50° C. and wherein step (b) is conducted at a temperature of between about 180° C. and about 200° C.

* * * * *

UNITED STATES PATENT AND TRADEMARK OFFICE
CERTIFICATE OF CORRECTION

PATENT NO. : 5,002,880
DATED : March 26, 1991
INVENTOR(S) : Robert W. Mason

It is certified that error appears in the above—identified patent and that said Letters Patent is hereby corrected as shown below:

In column 2, at line 9 after "is" and before "a", delete "suitable" and insert --suitably--; at line 33 after "esterase" delete "(EC)" and insert --(EC/--; and at line 65 after "porcine" and before "esterase" delete "line" and insert --liver--.

In column 3, at line 2 after "porcine" and before "esterase" delete "line" and insert --liver--.

Signed and Sealed this

Fifth Day of January, 1993

Attest:

DOUGLAS B. COMER

Attesting Officer

Acting Commissioner of Patents and Trademarks